United States Patent [19]

Kasztreiner et al.

[11] Patent Number: 4,748,175
[45] Date of Patent: May 31, 1988

[54] PYRIMIDO[5,4-B][1,4]OXAZINE DERIVATIVES AND PHARMACEUTICAL COMPOSITIONS CONTAINING THEM

[75] Inventors: Endre Kasztreiner; György Rabloczky; Nándor Makk; György Cseh; Mária Kuhár née Kürthy; Eszter Diesler; László Jaszlits; László Sebestyén; János Wellmann; Anikó Tegdes; Judit Sárossy née Kincsesy; Péter Mátyus; András Varró; László Szám, all of Budapest; Sarolta Végvári née Gyürki, Verocemaros, all of Hungary

[73] Assignee: Chinoin Gyogyszer Es Vegyeszeti Termekek Gyara Rt, Budapest, Hungary

[21] Appl. No.: 947,700

[22] Filed: Dec. 30, 1986

[30] Foreign Application Priority Data

Dec. 30, 1985 [HU] Hungary .............................. 5042/85

[51] Int. Cl.⁴ .................... A61K 31/535; C07D 498/04
[52] U.S. Cl. .................................... 514/230.5; 544/73; 544/105
[58] Field of Search ................... 544/73, 105; 514/232, 514/234, 236, 237, 239

[56] References Cited

PUBLICATIONS

Sazonov et al., Khim, Geterotsikl. Soedin., vol. 2 (1973) pp. 171–174.
Sazonov et al., Khim. Geterotsikl. Soedin, vol. 5 (1976) pp. 681–685.
Oda et al., Yakugaku Zasshi, vol. 93, No. 6 (1973) pp. 817–821.
Ito et al., Chem. Pharm. Bull., vol. 24, No. 6 (1976) pp. 1189–1196.
Sazonov et al., Khim. Geterotsikl. Soed., No. 9 (1972) pp. 1285–1288.
Sazonov et al., Khim. Geterotsikl. Soed., No. 12 (1973) pp. 1694–1696.
Sazonov et al., Khim. Geterotsikl. Soed., No. 3 (1978) pp. 391–396.
Sazonov et al., Chemical Abstracts, vol. 78 (1973) 124532e.
Sazonov et al., Chemical Abstracts, vol. 85 (1976) 108598v.
Oda et al., Chemical Abstracts, vol. 79 (1973) 66309v.
Ito et al., Chemical Abstracts, vol. 85 (1976) 123858y.

*Primary Examiner*—Richard L. Raymond
*Attorney, Agent, or Firm*—Karl F. Ross; Herbert Dubno; Jonathan Myers

[57] ABSTRACT

The invention relates to novel pyrimido [5,4-b][1,4]oxazine derivatives of the formula (I), and the acid addition salts thereof, pharmaceutical compositions containing them and a process for their preparation. In the formula (I)

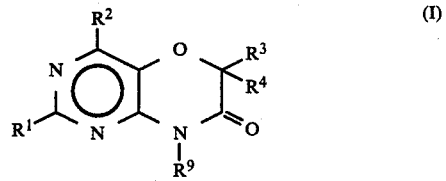

wherein
$R^1$ stands for a $C_{1-4}$ alkyl group;
$R^2$ stands for hydrogen or halogen or an azido group or an $-NR^5R^6$ group, wherein
  $R^5$ represents hydrogen or a benzyl group, or a $C_{1-4}$ alkyl group unsubstituted or substituted by a hydroxyl group,
  $R^6$ stands for hydrogen, an amino group, a $C_{3-6}$ cycloalkyl group, a straight or branched-chain $C_{1-4}$ alkyl group optionally substituted by a hydroxyl, mercapto, aminocarbonyl, furyl, 2-benzo[1,4]dioxanyl, di($C_{1-4}$ alkyl)amino group or by a phenyl or phenoxy group optionally mono- or polysubstituted by halogen or $C_{1-4}$ alkoxy group (s) or by a 6-membered, saturated nitrogen-containing heterocycle optionally containing an additional nitrogen or oxygen atom and optionally substituted by a $C_{1-4}$ alkyl or benzyl group; further
$NR^5R^6$ may also represents a 6-membered, saturated, nitrogen-containing heterocycle optionally containing an additional nitrogen or oxygen atom and optionally substituted by a $C_{2-4}$ alkoxycarbonyl or $C_{1-4}$ hydroxyalkyl group;
$R^3$ and $R^4$ are the same or different and stand for hydrogen or a $C_{1-4}$ alkyl group;
$R^9$ stands for hydrogen or a $C_{1-4}$ alkyl group unsubstituted or monosubstituted by an oxo, cyano, aminocarbonyl, $C_{2-5}$ alkoxycarbonyl, pyridiyl, morpholinocarbonyl, or phenyl group or mono- or polysubstituted by OH group(s), with the proviso that $R^2$ is different from chlorine, 4-morpholinyl and piperidyl group when $R^9$ stands for hydrogen; or
$R^2$ is different from chlorine and 4-morpholinyl group when $R^9$ stands for a methyl or benzyl group.

The compounds of the formula (I) are capable to increase the myocardial contractile force (the performance of the failing heart) and the coronary blood flow, thus they can therapeutically be used for the treatment of the chronic heart failure and coronary disturbances.

10 Claims, No Drawings

PYRIMIDO[5,4-B][1,4]OXAZINE DERIVATIVES AND PHARMACEUTICAL COMPOSITIONS CONTAINING THEM

This invention relates to novel pyrimido[5,4-b][1,4]oxazine derivatives of the formula (I),

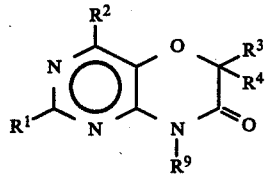

wherein
$R^1$ stands for a $C_{1-4}$ alkyl group;
$R^2$ stands for hydrogen or halogen or an azido group or an $—NR^5R^6$ group, wherein
  $R^5$ represents hydrogen or a benzyl group, or a $C_{1-4}$ alkyl group unsubstituted or substituted by a hydroxyl group,
  $R^6$ stands for hydrogen, an amino group, a $C_{3-6}$ cycloalkyl group, a straight or branched-chain $C_{1-4}$ alkyl group optionally substituted by a hydroxyl, mercapto, aminocarbonyl, furyl, 2-benzo[1,4]dioxanyl, di($C_{1-4}$) alkyl amino group or by a phenyl or phenoxy group optionally mono- or polysubstituted by halogen or $C_{1-4}$ alkoxy group(s) or by a 6-membered, saturated nitrogen-containing heterocycle optionally containing an additional nitrogen or oxygen atom and optionally substituted by a $C_{1-4}$ alkyl or benzyl group; further
  $NR^5R^6$ may also represent a 6-membered, saturated, nitrogen-containing heterocycle optionally containing an additional nitrogen or oxygen atom and optionally substituted by a $C_{2-4}$ alkoxycarbonyl or $C_{1-4}$ hydroxyalkyl group;
$R^3$ and $R^4$ are the same or different and stand for hydrogen or a $C_{1-4}$ alkyl group;
stands for hydrogen or a $C_{1-4}$ alkyl group unsubstituted or monosubstituted by an oxo, cyano, aminocarbony, $C_{2-5}$ alkoxycarbonyl, pyridyl, morpholinocarbonyl or phenyl group or mono- or polysubstituted by OH group(s), with the proviso that $R^2$ is different from a chlorine, 4-morpholinyl or piperidyl group when $R^9$ stands for hydrogen; or $R^2$ is different from a chloro or 4-morpholinyl group when $R^9$ stands for a methyl or benzyl group,
as well as their tautomers and tautomeric mixtures and acid addition salts thereof and pharmaceutical preparations containing these compounds.

According to another aspect of the invention, there is provided a process for the preparation of the new compounds of the formula (I) and acid addition salts thereof.

The novel pyrimido[5,4-b][1,4]oxazine derivatives of the invention possess valuable pharmacodynamic, mainly cardiovascular effects, particularly a cardiotonic (positive inotropic) action increasing the performance of deficient failing heart musculature. Some of these compounds also exert a favorable effect on the coronary circulation.

In a preferable group of the compounds of the formula (I): $R^1$ means a $C_{1-4}$ alkyl group; $R^2$ stands for $NR^5R^6$, wherein $R^5$ and $R^6$ are as defined above; $R^3$ and $R^4$ are independently hydrogen or a $C_{1-2}$ alkyl group; and $R^9$ stands for hydrogen or a $C_{1-4}$ alkyl group optionally substituted by an oxo, cyano, aminocarbonyl $C_{2-5}$ alkoxycarbonyl or one or more hydroxyl group(s).

The new pyrimido[5,4-b][1,4]oxazine derivatives of the invention belong to a ring system structurally less investigated hitherto.

Only a few articles referring to this type of compound are to be found in the literature. I. V. Sazonov and T. S. Safonov (Khim. Geterotsikl. Soed. 1972, 1285) described derivatives containing mainly an amino, acetamido or methyl group in the 2-position or a hydroxyl, methyl group or chlorine in the 4-position; and later (ibidem, 1973, 1694) compounds containing a double bond and ethoxycarbonyl group in the 6-position; thereafter, derivatives with a lower alkyl group in the 6-position (ibidem, 1976, 681); as well as compounds containing a morpholinyl group in the 4-position (ibidem, 1978, 391).

It is commonly known that the diseases affecting the cardiovascular system (e.g. chronic heart failure, myocardial infarction, hypertension) are the most frequent causes of death. Within this category the number of heart cases, mainly the number of patients suffering from chronic heart failure is continuously increasing. Today, most of these patients are treated with cardiac glycosides; however, it is well known that the use of these drugs is not safe because of the harmful side-effects (e.g. tachycardia and arrhythmia). Besides the setting-the dosage is difficult, as individual judgement and high care are required of from the physician since the therapeutic safety of these drugs is low. In addition, these drugs cannot be used for treating an acute or post-infarction heart failure.

In the last decade, the therapeutic damand became higher for drugs capable of increasing the performance of the failing myocardium without harmful side-effects after oral administration.

Several new cardiotonic compounds resulted from these investigations. The larger and more important groups may be characterized by some examples as follows.

Prenalterol [1-(4-hydroxyphenyl)-3-tertiary-butylamino-2-propanol] is a representative of the adrenergic $\beta_1$-agonists thoroughly studied in clinics. When given intravenously in acute cardiac insufficiency, this drug was very effective but the cardiac performance was not improved by it when chronic oral treatment was used [J. Cardiovasc. Pharm. 6, 491 (1984)].

Pirbuterol [1-(5-hydroxy-6-hydroxymethyl-2-pyridyl)-2-tertiary-butylaminoethanol], a drug stimulating both $\beta_1$ and $\beta_2$ adrenergic receptors, showed a favorable effect during oral treatment for some weeks but addiction was observed after a longer period [New Engl. J. Med. 305, 185 (1981)].

The mode of action of the bipyridine-type cardiotonics is different from that of the adrenergic $\beta$-agonists and not cleared up to the present. An outstanding member of this group, amrinone [3-amino-5-(4-pyridyl)-2(1H)-pyridinone] significantly increased the cardiac output of patients suffering from chronic heart failure and the resistance of the peripheral vessels was also diminished. However, the therapeutic suitability of amrinone is strongly limited by severe side-effects appearing in the blood picture [Am. J. Med. 72, 113 1983; Brit. J. Clin. Pharm. 17, 317 (1984)].

Sulmazole, a member of the imidazopyridines [2-(2-methoxy-4-methylsulfinylphenyl)-1H-imidazo[4,5-b]pyridine] also possesses a vasodilatory effect. In addition to the favorable target effect, relatively frequent side-effects of sulmazole were revealed by clinical tests [Annal. Cardiol. Anghiol. 33, 219 (1984)].

The biologic properties of the more important cardiotonics having an effect different from that of the cardiac glycosides indicate that an unaltered and continuous demand exists for newer drugs which can orally and chronically be used, which are free of side-effects and thus, can more safely be employed.

Now it has been found that the new pyrimido[5,4-b][1,4]oxazines of the formula (I), wherein $R^1$, $R^2$, $R^3$, $R^4$ and $R^9$ are as defined above, fairly satisfy the above-defined therapeutical demands.

According to the invention, the compounds of the formula (I) are prepared by (a) reacting a compound of the formula (II),

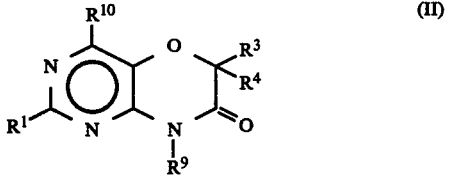

wherein $R^1$, $R^3$ and $R^9$ are as defined for the formula (I) and $R^{10}$ stands for a leaving group with an amine of the formula $HNR^5R^6$, optionally having a protecting group, wherein $R^5$ and $R^6$ are as defined for formula (I), to obtain compounds of the formula (I), wherein $R^2$ stands for an $-NR^5R^6$ group (wherein $R^5$ and $R^6$ are as defined above) and $R^1$, $R^3$, $R^4$ and $R^9$ are as defined above or (b) diazotizing a compound of the formula (I), wherein $R^1$, $R^3$, $R^4$ and $R^9$ are as defined for formula (I) and $R^2$ stands for a hydrazino group, to obtain compounds of the formula (I), wherein $R^2$ stands for an azido group and $R^1$, $R^3$, $R^4$ and $R^9$ are as defined above, or (c) reacting a compound of the formula (I), wherein $R^1$, $R^2$, $R^3$ and $R^4$ are as defined for formula (I) and $R^9$ stands for hydrogen, with 2,3-epoxypropanol to obtain compounds of formula (I), wherein $R^1$, $R^2$, $R^3$ and $R^4$ are as defined above and $R^9$ means a 2,3-dihydroxypropyl group, and, if desired, reacting a compound of the formula (I), optionally containing a protective group and obtained by processes (a) or (b), wherein $R^1$, $R^2$, $R^3$ and $R^4$ are as defined for formula (I) and $R^9$ stands for hydrogen, with a compound of the formula $R^9X$ optionally containing a protective group, wherein $R^9$ is as defined for formula (I) except hydrogen and X means a leaving group; and/or, if desired, removing the protective group from a product obtained by any one of processes (a) to (c); and/or, if desired, transforming a compound of the formula (I) obtained in the above way to an other compound of the formula (I); and/or, if desired, transforming a base of the formula (I), obtained in the above way, by treating it with an acid, to an acid addition salt; and/or, if desired, transforming an acid addition salt into another acid addition salt; and/or, if desired, liberating a free base of the formula (I) from its acid addition salt.

According to the literature definition [T. A. Geissman: Principles of Organic Chemistry, 3rd edition; Editor W. H. Freeman, London, 1968], $R^{10}$ and X as "leaving groups" are moieties which are easy to cleave by nucleophilic agents. Such groups are e.g. halogens; sulfonyloxy groups such as lower alkanesulfonyloxy and optionally substituted benzenesulfonyloxy groups; as well as lower alkanesulfonyl and -sulfinyl groups, e.g. methanesulfonyl group.

In the processes of the invention, chlorine or 4-toluenesulfonyloxy group as $R^{10}$, whereas chlorine or bromide as X are particularly preferred.

A preferred embodiment of process (a) of the invention comprises reacting a compound of the formula (II), wherein $R^{10}$ is chlorine, with an $HNR^5R^6$ amine. This reaction is carried out in an inert organic solvent or diluent, in the presence of an acid binding agent. Lower aliphatic alkanols, e.g. n-butanol or an aromatic hydrocarbon, e.g. benzene, are suitably used as solvents. An excess of the amine may conveniently be used as an acid binding agent though a tertiary organic amine, e.g. triethylamine, or an inorganic base such as potassium carbonate may also be employed. This reaction is carried out at 50° to 150° C., suitably at the boiling point of the solvent.

According to another preferred embodiment of process a) of the invention, a compound of the formula (II), wherein $R^{10}$ is an arylsulfonyloxy, e.g. the 4-toluenesulfonyloxy group, is reacted with a $HNR^5R^6$ amine. The components are similarly reacted in an organic solvent or diluent, in the presence of an acid binding agent. It is suitable to use an ester-type solvent such as ethyl acetate and an excess of the amine or an organic tertiary amine, e.g. triethylamine, or an inorganic base such as potassium carbonate as acid binding agent. This reaction is established between 10° C. and the boiling point of the reaction mixture.

When using process (b) of the invention, a compound of the formula (I), wherein $R^2$ is a hydrazino group, is treated with sodium nitrite in an aqueous acetic acid medium under the known conditions of diazotization at 0° to 5° C.

A preferred embodiment of process (c) of the invention comprises reacting a compound of the formula (I), wherein $R^9$ is hydrogen, with 2,3-epoxypropanol in a solvent, in the presence of a quaternary ammonium salt as catalyst. It is preferable to use an aromatic hydrocarbon, e.g. benzene as solvent and tetrabutylammonium bromide as catalyst and to work at the boiling point of the solvent, e.g. benzene.

The reaction mixture obtained from the above processes may be worked up in a known way, e.g. by evaporation under vacuo, optionally after filtering out the inorganic salts and/or catalyst, by mixing the residue with water, alkalizing and separating the thus-obtained product by filtration or extraction. If desired, the thus-obtained base of the formula (I) can be purified and/or transformed to an acid addition salt which can be purified, if desired, by recrystallization.

A compound of formula (I), obtained in process (a) or (b), wherein $R^9$ is hydrogen, may be transformed, if desired, to a compound of the formula (I), wherein $R^9$ is different from hydrogen. This transformation is preferably carried out in such a way that the compound of the formula (I) containing hydrogen as $R^9$ is reacted with a compound of the formula $R^9X$, wherein X preferably means chlorine or bromine or 4-toluenesulfonyloxy group, in the presence of a solvent and an acid binding agent. Ketones such as acetone, preferably methyl ethyl ketone, or lower alkanols, e.g. ethanol or isopropanol, are suitable solvents. As a base, an alkali metal alkoxide prepared from the alkanol solvent may be used; when employing a ketone as solvent, the use of potassium carbonate for acid-binding is particularly advantageous. This reaction is suitably carried out at the boiling point of the solvent.

It is obvious for one skilled in the art that in some cases, the compounds used in processes (a) to (c) should be provided with protective groups for avoiding side reactions. Such protective groups are commonly known. Out of these, the benzyl group is particularly favorable in the preparation of the compounds of the invention as it can easily be removed by catalytic hydrogenolysis.

The bases of the general formula (I) may be transformed in a known way to acid addition salts which are suitably pharmaceutically acceptable, e.g. by dissolving the base in a suitable organic solvent and adding the appropriate acid or a solution of this acid in a suitable organic solvent. The salt is isolated by filtering or by evaporating under vacuo then, if desired, it is purified in a known way, e.g. by recrystallization. Non-toxic inorganic acids, e.g. hydrochloric, hydrobromic, sulfuric or phosphoric acid, or non-toxic organic acids such as acetic, tartaric, maleic or fumaric acid are preferable acid components.

When the acid component is an inorganic mineral acid, then a lower alkanol, e.g. ethanol or isopropanol, or acetone is suitable used as solvent. When the acid is organic, then the above solvents or an ether such as ethyl or isopropyl ether may also be used.

In the starting substances of the formula (II), required for process (a) of the invention, $R^{10}$ preferably means chlorine or a 4-toluenesulfonyloxy group. A part of the compounds, wherein $R^{10}$ means chlorine, are known [see, e.g. Khim. Geterotsikl. Soed. 1972, 1985]. The compounds of the formula (II) hitherto not described may be prepared by methods known from the literature or analogously to known methods.

The compounds of the formula (II) containing an alkane- or arylsulfonyloxy group as $R^{10}$ are new and may be prepared e.g. by reacting a compound of the formula (I), wherein $R^2$ is a hydroxyl group, in a known manner with the appropriate alkane- or arylsulfonyl chloride in a basic medium. This method will be illustrated in Example 23.

The compounds of the formula (II) containing a methylsulfonyl group as $R^{10}$ are also new and may be prepared e.g. by oxidizing a compound of the formula (II), wherein $R^{10}$ is a methylthio group, in a known manner. This method will be illustrated in Example 26. A part of the appropriate methylthio compounds are known (Khim. Geterotsikl. Soed 1973, 171). The new methylthio compounds may be prepared by known methods or analogously to known methods.

The majority of the compounds of the formula $R^9X$, required for the subsequent (additional) transformation of compounds of the formula (I) containing hydrogen as $R^9$, are known (see e.g. E. H. Rodd: Chemistry of Carbon Compounds, Elsevier Publishing Co., London, 1951, 615). The new $R^9X$ compounds may be prepared by known methods or analogously to known methods.

As mentioned above, the compounds of the invention possess valuable biological, particularly cardiotonic action.

The myocardial contractile force (with an international abbreviation: MCF) increasing effect of the compounds of the invention was proved by using in vivo tests and methods as follows.

METHODS (A) Investigation on anaesthetized cats

The animals were intravenously (i.v.) anaesthetized by 30 mg/kg of pentobarbital-sodium. After arranging the artificial respiration, the chest and pericardium were opened. A strain gauge arch was sutured onto the epicardial surface of the left ventricle [J. Pharm. Exp. Ther. 90, 26 (1947)]. The blood pressure was measured by a catheter inserted to the femoral artery and joined to a P 23 Db pressure transducer and electromanometer. The test compounds were administered either i.v. through a femoral vein cannule, or intraduodenally (i.d.) through the duodenum cannule. At the beginning of the experiment, 0.2 µg/kg of isoproterenol (IS) was i.v. given as an internal standard for checking the myocardial reactivity. Namely, the value of the peak MCF response can also be altered according to the individual animals in the case of each positive inotropic agent. Thus, IS was not used as a real reference drug.

The MCF responses were expressed in the percentage changes of the initial value: the effect on MCF of 5 mg/kg i.v. of the test compound was compared to that of 0.2 µg/kg i.v. of IS. The results are summarized in Table 1.

TABLE 1

MCF-increasing effect of compounds of formula (I) in open-chest, anaesthetized cats after i.v. administration of 5 mg/kg of the compound

| Compound Example No. | Increase in MCF as % of the initial value | Effectivity as compared to 0.2 µg/kg i.v. of IS |
|---|---|---|
| 22 (23, 26) | 70 | 1.2 |
| 11 | 83 | 1.2 |
| 60 | 51 | 1.2 |
| 56 | 100 | 1.5 |
| 57 | 45 | 1.3 |
| 27 | 130 | 3.0 |
| 37 | 55.5 | 1.2 |
| 29 | 40 | 0.9 |
| 66 | 58.3 | 0.82 |
| 67 | 37 | 1.8 |
| 69 | 66 | 0.87 |
| 73 | 50 | 0.86 |

Thus, the compounds of the invention possess an MCF-increasing effect similar to or higher than that of IS. Being a strong adrenergic β-stimulant, IS caused a measurable MCF increase in an i.v. dose of as low as 0.2 µg/kg. Further on, IS elicited a short-lasting and completely reversible MCF response and did not influence the blood circulation parameters. Remarkably, the heart rate was hardly or not at all increased by the compounds of the invention of Table 1.

The effect of several compounds was also studied after i.d. administration. Compounds 27 and 37 showed a strong positive inotropic action in a dose of both 20 mg/kg and 5 mg/kg. A strong and long-lasting MCF increase was observed after even a 1 mg/kg dose of compound 22.

(B) Investigation on anaesthetized dogs

The animals were i.v. anaesthetized by 35 mg/kg of pentobarbital-sodium. After opening the chest and pericardium, the lower ascending part of the left circumflex coronary artery was prepared and fitted with an electromagnetic flow probe for measuring the blood flow in the coronary artery. A strain gauge arch was placed onto the area supplied by this coronary artery for measuring the MCF. For determining the systemic blood pressure a femoral arterial cannule, for i.v. drug administration a femoral venous cannule was used. The dp/dt value was calculated from the pressure measured by a Millar type pressure transducer introduced to the left ventricle. All parameters were registered on a Beckman R 12 8-channel dynograph.

(C) Investigation on conscious cats

These animals were used according to either the method of Rabloczky and Mader ("Measurement of Systemic and Pulmonary Arterial Pressure in Conscious Animals", lecture on Congress of the International Union of Pharmacologists, Budapest, 1980) or to some modification thereof. The aorta and pulmonary artery were chronically catheterized for measuring both blood pressures. In the modification, the right ventricle was also catheterized for determining the $dp/dt_{max}$ value.

The positive inotropic and coronary-dilating activity of the compounds of the invention are shown by the results obtained on the detailed study of compounds 22, 27 and 37 by using the above methods.

STUDY ON COMPOUND 22

The positive inotropic effect of this compound could be observed in open-chest anaesthetized dogs after an i.v. administration of doses as low as 0.025 to 1.6 mg/kg. The strength and duration of the MCF increase were dose-dependent. The positive inotropic and coronary-dilating effect of 0.2, 0.4 and 0.8 mg/kg i.v. doses of this compound were compared to those of 0.5, 1.0 and 2.0 mg/kg of amrinone [5-amino-(3,4'-bipyridin)-6(1H)-one]. In this dose interval, compound 22 only elicited a dose-dependent MCF-increasing effect. The action of 2 mg/kg of amrinone was not more effective than that of 0.4 mg/kg of compound 22. Obviously, the positive inotropic effect of both compounds was promoted by the increase in the coronary blood flow; however, the MCF-increasing effect was more lasting than the coronary one.

The favorable action of copound 22 on the heart muscle was also proved after i.d. administration. MCF was increased by 35 to 40% after an 1 mg/kg dose without any change in the coronary flow. The MCF effect of compound 22 was at least 5 times higher than that of amrinone.

In anaesthetized open-chest dogs, after an acute myocardial ischaemia, the positive inotropic action of amrinone significantly decreased, whereas that of compound 22 remained statistically unchanged. An 0.8 mg/kg i.v. dose of compound 22 significantly diminished the negative inotropic effect of 0.2 IU/kg of vasopressin, and even reversed the coronary-constricting effect of the latter. Thus, compound 22 could prevent the development of a chemically induced ischaemia.

On administering 0.5, 2.0, 4.0 and 8.0 mg/kg oral doses of compound 22 to chronically catheterized conscious cats, the systemic arterial pressure and heart rate remained practically unchanged but MCF was significantly increased after each dose. The higher was the dose, the longer lasted the positive inotropic effect. The peak increase in $dp/dt_{max}$ was about 60%.

The positive inotropic effect of compound 22 remained unchanged after a pre-treatment with an adrenergic $\beta$-blocking agent, a histamine H-2 antagonist or reserpine.

STUDY ON COMPOUND 27

This substance was given in 1 mg/kg i.v. or 5 mg/kg i.d. doses to anaesthetized open-chest dogs.

A 1 mg/kg i.v. dose increased the MCF by 40%, the coronary flow by 20% and elicited only a slight tachycardia (of 10%) and a slight decrease (of 10%) in the systemic systolic arterial blood pressure (the diastolic pressure was decreased by 20%). The half-life of the MCF effect proved to be 10 minutes. The coronary response remained unchanged for 20 minutes.

After a 5 mg/kg i.d. dose, the MCF increase was 30% and remained unchanged for 30 minutes.

STUDY ON COMPOUND 37

This substance was given in 0.5 and 1.0 mg/kg i.v. or 5 mg/kg i.d. doses to anaesthetized open-chest dogs. A 0.5 mg/kg i.v. dose increased the MCF by 56%, the coronary flow by 34%, elicited only a very slight tachycardia (of 6 to 7%) and a slight decrease (of 10 to 15%) in the systemic arterial blood pressure.

A 1.0 mg/kg i.v. dose increased the MCF by 46% for 10 minutes, the coronary flow by 20% for 10 minutes, increased the heart rate by only 13% (for 5 minutes) and decreased the systemic arterial blood pressure by 20%.

After a 5 mg/kg i.d. dose, the MCF increase was about 30% persisting for 60 minutes.

BIOCHEMICAL-PHARMACOLOGICAL INVESTIGATIONS

The following study was performed for exploring the action of compound 22 on various enzymes, particularly on the membrane-bound enzymes of the heart muscle cells.

EFFECT OF COMPOUND 22 ON THE NA-K-ATP-ASE AND NADH OXYDASE ENZYMES

Sarcolemma preparations were made according to D. M. Bers [Biochem. Biophys. Acta 555, 131 (1979)]. NADH-dichlorophenol-reductase was determined by using a Centrifi-CHEM ® enzyme-analyzer. The activity of Na-K-ATP-ase was measured in 50 mM Tris-HCl (at pH 7.5). Ouabain, used as reference substance, strongly inhibited Na-K-ATP-ase and slightly the indophenol-reductase at $10^{-7}M$ concentration. The activity of these enzymes was not altered by even a $10^{-4}M$ concentration of compound 22.

EFFECT OF COMPOUND 22 ON THE Ca-ATP-ASE MAINLY REGULATING THE OUTWARD FLOW OF $Ca^{2+}$ THROUGH THE SARCOLEMMA

The activity of this enzyme was measured according to Mc Namara [J. Biochem. 75, 795 (1974)].

The enzyme activity was changed from a control value of $K_a=0.83$ mM to $K_a=1.8$ mM by a $10^{-4}M$ concentration of compound 22. Thus, the effect was slight.

In another experiment, compound 22 was given in a 2 mg/kg i.p. daily dose for 5 days. After taking an ex vivo sample, the enzyme activity was found as decreased by 30% (as corrected to 1 g of heart tissue).

EFFECT OF COMPOUND 22 ON THE $^{45}Ca^{2+}$ UPTAKE INTO THE SARCOPLASMA RETICULUM IN THE PRESENCE OF ATP

The method of S. Harigaya [Circ. Res. 25, 761 (1969)] was used.

The Ca-uptake was inhibited by 25% by $5 \times 10^{-3}$M concentration of compound 22, similarly to the inhibition by $10^{-2}$M concentration of caffeine.

EFFECT OF COMPOUND 22 ON THE CYCLIC ADENOSINE MONOPHOSPHATE cAMP CONTENT OF THE HEART MUSCLE CELLS

[For the method, see: Amer. J. Sci. 179, 807 (1973); and Clin. Chim. Acta 66, 221 (1974)].

Rats were given i.p. 5 mg/kg of compound 22, then sacrified at 0, 2, 5, 15 and 30 minutes, respectively, after treatment. The hearts were homogenized with trichloroacetic acid and the cAMP content was measured by a radioactive method, by using a specific binding protein. The cAMP content of the heart was not significantly altered by compound 22.

EFFECT OF COMPOUND 22 ON THE PHOSPHODIESTERASE (PDE) ACTIVITY OF THE HEART MUSCLE $PDE_1$ was prepared according to Sharma [Adv. Cycl. Nucl. Res. 10, 187 (1979)].

$PDE_2$ [Adv. Cycl. Nucl. Res. 5, 159 (1975)] and $PDE_3$ [Adv. Cycl. Nucl. Res. 10, 69 (1979)] were isolated according to Thompson et al. The enzyme activity was determined by using the same authors' method [Adv. Cycl. Nucl. Res. 5, 161 (1975)].

None of the PDE subtypes was influenced by a 100 $\mu$M concentration of compound 22.

According to the above experiments, compound 22 did not produce either the typical enzyme effects of the cardiac glycosides (on Na-K-ATP-ase or NADH-oxydase) or the characteristic effect of vegetative receptor stimulants (increase in the cAMP content, i.e. effect on the adenylate-cyclase enzyme activity).

Unlikely to some xanthine derivatives of the new bipyridine-type compounds (e.g. amrinone), compound 22 did not alter the activity of any of the PDE enzymes.

The acute toxicity data of compound 22 are given as $LD_{50}$ values in Table 2.

TABLE 2

| | $LD_{50}$ values in mg/kg | |
|---|---|---|
| | Male | Female |
| Mice | i.v. 323.9 | 339.89 |
| | (312.08–336.29) | (331.7–348.2) |
| | i.p. 572.23 | 573.08 |
| | (524.17–624.7) | (520.09–631.47) |
| | p.o. 1355.9 | 1419.6 |
| | (1192.7–1541.4) | (1313.3–1534.4) |
| Rats | i.v. 253.45 | 232.3 |
| | (235.18–273.14) | (209.4–257.7) |
| | i.p. 315.0 | 260.0 |
| | (277.28–357.8) | (201.55–335.4) |
| | p.o. 829.6 | 809.9 |
| | (722.5–952.6) | (724.7–901.4) |

Note: The values in parentheses are the confidence limits. Thus, the acute toxicity of compound 22 is low.

On the basis of the pharmacological results, the compounds of the invention can be used for treating cardiovascular diseases, mainly for increasing the performance of the failing heart musculature and improving the coronary circulation (flow). Their toxicity is in general low. When taken together these properties, a broad spectrum of effects and therapeutic safety are provided.

For therapeutical use, an indicated daily dose is in the range from about 0.2 mg/kg to 250 mg/kg, preferably from 0.2 mg/kg to 50 mg/kg optionally administered in divided daily doses with consideration of the absorption conditions.

For therapeutical use, the active compounds of the invention are suitably formulated to pharmaceutical compositions by mixing them non-toxic, inert, solid or liquid carriers and/or additives which are appropriate for enteral or parenteral administration and are commonly used in the pharmaceutical industry. E.g. water, gelatin, lactose, starch, pectin, magnesium stearate, stearic acid, talc and vegetable oils are suitable carriers. As additives preserving wetting (surface active), emulsifying or dispersing, buffering and aromatizing agents may be used.

By using the above carriers and additives, the active substances of the invention may be formulated to the usual pharmaceutical compositions, e.g. solid forms (such as tablets, capsules, pills and suppositories) or liquid forms (such as aqueous or oily solutions, suspensions, emulsions, syrups) as well as to injectable solutions, suspensions and emulsions.

The invention also relates to the pharmaceutical compositions containing a compound of the general formula (I) or a pharmaceutically acceptable acid addition salt thereof as active ingredient; as well as to a process for preparing these compositions.

The invention is illustrated in detail by the following non-limiting Examples.

EXAMPLE 1

4-(4-Ethoxycarbonyl-1-piperazinyl)-2-methyl-6,7-dihydro-8H-pyrimido[5,4-b][1,4]oxazin-7-one A mixture containing 1 g of 4-chloro-2-methyl-6,7-dihydro-8H-pyrimido[5,4-b][1,4]oxazin-7-one (Khim. Geterotsikl. Soed. 1976, 681), 10 ml of n-butanol and 1.58 g of 1-ethoxycarbonylpiperazine is refluxed under protection against moisture and carbon dioxide, then evaporated. The residue is triturated with water and the product precipitated at 0° to 4° C. is filtered, washed with water and ether and dried to give 1.4 g (87%) of product, m.p.: 197°–198° C.

EXAMPLE 2

2,6-Dimethyl-4-[4-(2-hydroxyethyl)-1-piperazinyl]-6,7-dihydro-8H-pyrimido[5,4-b][1,4]oxazin-7-one A mixture containing 0.86 g of 4-chloro-2,6-dimethyl-6,7-dihydro-8H-pyrimido[5,4-b][1,4]oxazin-7-one (Khim. Geterotsikl. Soed. 1972, 1285), 20 ml of n-butanol and 1.04 g of 1-hydroxyethylpiperazine is refluxed for 7 hours, then evaporated. After adding 20 ml of water, the residue is extracted with ethyl acetate. The organic solution is dried and evaporated. After recrystallizing the residue from ethyl acetate, 0.90 g of product is obtained, m.p.: 160°–161° C.

The compounds of the formula (I), wherein $R^1$ is a methyl group and $R^9$ is hydrogen, shown in Table 3, were prepared analogously to the process described in Example 1 or 2.

TABLE 3

| Example No. | R² | R³ | R⁴ | Method (No. of type example) | Yeild % | M.p. (base) °C. |
|---|---|---|---|---|---|---|
| 3 | Cyclopropylamino | H | H | 1 | 60 | 224–226ˣ |
| 4 | 2-Hydroxyethylamino | CH₃ | H | 1 | 49 | 195–197 |
| 5 | bis(2-Hydroxyethyl)-amino | CH₃ | H | 2 | 57 | 155–157 |
| 6 | N—Methyl-N—(2-hydroxyethyl)-amino | H | H | 1 | 92 | 156–158 |
| 7 | 2-Mercaptoethylamino | CH₃ | H | 2 | 52 | 185–187 |
| 8 | N—Methyl-N—(aminocarbonylmethyl)-amino | H | H | 1 | 82 | 255–257 |
| 9 | [2-(4-Fluorophenoxy)-ethyl]-amino | CH₃ | H | 1 | 64 | 140–141 |
| 10 | [2-(3,4-Dimethoxyphenyl)-ethyl]-amino | CH₃ | H | 1 | 74 | 148–150 |
| 11 | N—Benzyl-N—(2-hydroxyethyl)-amino | H | H | 1 | 77 | 136–138 |
| 12 | [2-(4-Morpholinyl)-ethyl]-amino | CH₃ | H | 2 | 53 | 152–154 |
| 13 | [2-(4-Morpholinyl)-ethyl]-amino | CH₃ | CH₃ | 2 | 71 | 148–149 |
| 14 | 4-(2-Hydroxyethyl)-1-piperazinyl | H | H | 1 | 68 | 187–188 |
| 15 | (2-Furlymethyl)-amino | CH₃ | H | 1 | 54 | 142–144 |
| 16 | (2-Benzo[1,4]dioxanyl)-methylamino | H | H | 2 | 37 | 165–167ˣ |
| 17 | 4-Chlorobenzylamino | CH₃ | H | 1 | 83 | 171–173 |
| 18 | 2-Phenoxyethylamino | CH₃ | H | 1 | 57 | 162–164 |

Note:
ˣHydrochloride

EXAMPLE 19

4-(2-Hydroxyethyl)amino-2-methyl-6,7-dihydro-8H-pyrimido[5,4-b][1,4]oxazin-7-one A solution containing 2 g of the product of Example 11 in 60 ml of methanol is hydrogenated on 1.2 g of 10% of palladium-on-charcoal catalyst at atmospheric pressure and room temperature, then the mixture is boiled for 15 minutes and filtered as hot. The filtrate is evaporated to 35 ml, cooled at 0° to 4° C., the precipitate is filtered and washed with methanol to give 1.26 g (90%) of the product, m.p.: 192°–194° C.

EXAMPLE 20

4-(2-Diethylaminoethyl)amino-2-methyl-6,7-dihydro-8H-pyrimido[5,4-b][1,4]oxazin-7-one dihydrochloride A mixture containing 2 g of 4-chloro-2-methyl-6,7-dihydro-8H-pyrimido[5,4-b][1,4]oxazin-7-one, 1.52 g of triethylamine 1.16 g of 2-diethylaminoethylamine and 50 ml of abs. benzene is refluxed while stirring for 20 hours, then evaporated. After adding water to the residue, the pH is adjusted to 3 and the mixture is extracted with chloroform. The aqueous phase is alkalized to pH 9, extracted with chloroform, the latter organic phase is washed with water, dried and evaporated. The oily residue is taken up in ethanol and ethanolic hydrogen chloride solution is added. The precipitate is filtered to give 0.56 g (16%) of the product, m.p.: 252°–255° C.

EXAMPLE 21

2-Methyl-4-[2-(1-piperidyl)-ethyl]-amino-6,7-dihydro-8H-pyrimido[5,4-b][1,4]oxazin-7-one dihydrochloride According to Example 20, starting from 1.23 g of 2-(1-piperidyl)-ethylamine, 0.91 g (25%) of the product is obtained, m.p.: 135°–140° C.

EXAMPLE 22

2-Methyl-4-[2-(4-morpholinyl)-ethyl]-amino-6,7-dihydro-8H-pyrimido[5,4-b][1,4]oxazin-7-one dihydrochloride According to Example 20, a mixture containing 1 g of 4-chloro-2-methyl-6,7-dihydro-8H-pyrimido[5,4-b][1,4]oxazin-7-one, 1.01 g of triethylamine and 0.65 g of 2-(4-morpholinyl)-ethylamine is refluxed for 40 hours to give 0.46 g (25%) of the product, m.p.: 233°–237° C. (with decomposition).

EXAMPLE 23

2-Methyl-4-[2-(4-morpholinyl)-ethyl]-amino-6,7-dihydro-8H-pyrimido[5,4-b][1,4]oxazin-7-one dihydrochloride Method (A)

A mixture containing 50 g of 2-methyl-4-(4-toluenesulfonyloxy)-6,7-dihydro-8H-pyrimido[5,4-b][1,4]oxazin-7-one, 20.73 g of anhydrous potassium carbonate, 19.5 g of 2-(4-morpholinyl)-ethylamine and 1250 ml of abs. ethyl acetate is stirred at 20° C. for 72 hours, then the insoluble fraction is filtered. The filtrate is extracted with 1N aqueous hydrochloric acid, the pH of the aqueous phase is adjusted to 4 to 5 and the solution is extracted with dichloromethane. Then the pH of the aqueous phase is adjusted to 9 to 10 and it is extracted with dichloromethane. The combined organic solution obtained from the latter extraction is dried and evaporated. The remained crude base is dissolved in acetone, then abs. ethanolic hydrogen chloride solution is added under cooling. The precipitate is filtered and washed with acetone to give 27.31 g (50%) of product, m.p.: 233°–237° C. (with decomposition).

Method (B)

A mixture containing 5 g of 2-methyl-4-(4-toluenesulfonyloxy)-6,7-dihydro-8H-pyrimido[5,4-b][1,4]oxazin-7-one, 2.99 g of 2-(4-morpholinyl)-ethylamine, 9.11 g of triethylamine and 130 ml of abs. ethyl acetate is boiled for 5 hours, then filtered and the filtrate is evaporated. The residue is mixed with water, the pH is adjusted to 2, the solution is extracted with ethyl acetate and the aqueous phase is adjusted to pH 5. Further on, the working-up is carried out as described in method (A) to give 3.28 g (60%) of product, m.p.: 233°–237° C. (with decomposition).

The fumarate of the desired base is prepared as follows:

To a solution containing 1 g of crude base [prepared according to method (A) or (B)] in 9 ml of ethanol, 0.2 g of fumaric acid dissolved in 5 ml of hot ethanol is portionwise added at 70° C., then the mixture is cooled and kept at 0° to 4° C. overnight. The fumarate of the desired base, containing the base in a 2:1 mole ratio as related to fumaric acid, is obtained in a nearly quantitative yield, m.p.: 215°–216° C.

Analysis: Calculated for $C_{30}H_{42}N_{10}O_{10}$ (molecular weight: 702.72): C 51.27; H 6.03; N 19.93%; found C 51.63; H 5.96; N 19.66%.
The fumaric acid content was found to be 16.50% (calculated 16.52%).

2-Methyl-4-(4-toluenesulfonyloxy)-6,7-dihydro-8H-pyrimido[5,4-b][1,4]oxazin-7-one, the common starting material of both method A) and B) may be prepared e.g. as follows:

To a solution containing 135.8 g of 4-hydroxy-2-methyl-6,7-dihydro-8H-pyrimido[5,4-b][1,4]oxazin-7-one (Khim. Geterotsikl. Soed. 1976, 681) in 1205 ml of 1N aqueous sodium hydroxide, a solution of 157.2 g of 4-toluenesulfonyl chloride in 450 ml of acetone is dropped at room temperature under stirring for 3 hours and then the mixture is stirred at room temperature for 5 hours. The crystals are filtered, washed with water and taken up in 1800 ml of acetone. The precipitate (i.e. the unchanged starting material) is filtered out and washed with acetone. The filtrate is evaporated, the crystals are filtered, washed with a little acetone and dried to give 123.2 g (49%) of the product, m.p.: 185°–186° C.

The compounds of Table 4 were essentially prepared according to method (A) of Example 23.

| Example No. | $R^2$ | Yield % | M.p. °C. salt form |
|---|---|---|---|
| 24 | 2-(2-Methyl-4-morpholinyl)-ethylamino | 18 | 186–190 (dihydrochloride) |
| 25 | 2-(4-Methyl-1-piperazinyl)-ethylamino | 69 | 193–195 (diemaleate) |

EXAMPLE 26

2-Methyl-4-[2-(4-morpholinyl)-ethyl]-amino-6,7-dihydro-pyrimido[5,4-b][1,4]oxazin-7-one dihydrochloride A mixture of 0.34 g of 4-methanesulfonyl-2-methyl-6,7-dihydro-8H-pyrimido[5,4-b][1,4]oxazin-7-one and 0.40 g of 2-(4-morpholinyl)-ethylamine is heated at 75° to 80° C. for 10 minutes and after cooling taken up in 8 ml of 1N sodium hydroxide solution and exhaustively extracted with dichloromethane. The organic solution is extracted with water, dried, filtered and evaporated to give 0.21 g (52.5%) of the crude base which can be transformed to the dihydrochloride as described in Example 22 or 23. The crude base can be crystallized by mixing thoroughly with ethanol or acetone, m.p.: 143°–145° C.

4-Methanesulfonyl-2-methyl-6,7-dihydro-8H-pyrimido[5,4-b][1,4]-oxazin-7-one, i.e. the starting material can be prepared e.g. as follows:

2 ml of 30% hydrogen peroxide are added to a solution containing 0.83 g of 2-methyl-4-methylthio-6,7-dihydro-8H-pyrimido[5,4-b][1,4]oxazin-7-one (Khim. Geterotsikl. Soed. 1973, 171) in 8 ml of acetic acid and heated at 60° C. under stirring for 3 hours. The solution is evaporated to dryness. The traces of acetic acid are removed and the remaining white crystalline material is triturated with 5 ml of water. The pH of the mixture is adjusted to 6.5, the precipitate is filtered and dried to give 0.36 g (38%) of product, i.e. the starting material of Example 26, m.p.: 211° C.

EXAMPLE 27

4-[(4-Benzyl-2-morpholinyl)-methyl]-amino-2-methyl-6,7-dihydro-8H-pyrimido[5,4-b][1,4]oxazin-7-one dihydrochloride dihydrate Method (A)

A suspension containing 16 g of 2-methyl-4-(4-toluenesulfonyloxy)-6,7-dihydro-8H-pyrimido[5,4-b][1,4]oxazin-7-one (Example 23), 8.93 g of 2-aminomethyl-4-benzylmorpholine and 6.6 g of anhydrous potassium carbonate in 400 ml of abs. ethyl acetate is stirred at room temperature for 80 hours, then the insoluble part is filtered and the filtrate is extracted with 1N hydrochloric acid. The pH of the aqueous phase is adjusted to 7 by 1N sodium hydroxide solution and extracted with ether. The ethereal solution is dried and evaporated. The crude residue is dissolved in abs. ethanol and a calculated amount of abs. ethanolic hydrogen chloride solution is portionwise added. After cooling at 0° to 4° C., the precipitate is filtered, washed with cold abs. ethanol and dried to give 2.33 g (15%) of the product, m.p.: 196°–199° C.

Method (B)

A suspension containing 3 g of 2-methyl-4-(4-toluenesulfonyloxy)-6,7-dihydro-8H-pyrimido[5,4-b][1,4]oxazin-7-one (Example 23), 1,85 g of 2-aminomethyl-4-benzylmorpholine, 5.43 g of triethylamine and 80 ml of abs. ethyl acetate is boiled for 8 hours while stirring, then evaporated. The residue is mixed with 50 ml of water and the pH is adjusted to 1 to 2 by adding 1N hydrochloric acid. After extracting with ethyl acetate, the pH of the aqueous phase is adjusted to 7 by 1N sodium hydroxide solution and extracted with ether. Further on, method (A) is followed to give 1.0 g (13%) of the product, m.p.: 195°–198° C.

2-Aminomethyl-4-benzylmorpholine, the common starting material of both method (A) and (B) can be prepared e.g. as follows:

Step (a): 4-Benzyl-2-phthalimidomethylmorpholine 50.2 g of potassium phthalimide are added to 61.2 g of 4-benzyl-2-chloromethylmorpholine [Synth. Com. 10, 59 (1980)] dissolved in 150 ml of abs. dimethylformamide and the mixture is boiled under stirring for 6 hours. After cooling, the crystals are filtered, washed with dimethylformamide and then with cold water and dried to give 68.95 g (76%) of the product, m.p.: 130°–132° C.

Step (b): 2-Aminomethyl-4-benzylmorpholine dihydrochloride

A mixture containing 19.3 g of the product of Step (a) and 38 ml of concentrated hydrochlorid acid is boiled under stirring for 10 to 14 hours. After cooling, the phthalic acid precipitate is filtered and the solution is extracted with ethyl acetate. The aqueous phase is evaporated to dryness and the residue is triturated with abs. ethanol. The crystals are filtered, washed with abs. ethanol and dried to give 10.3 g (65%) of the product, m.p.: 244°–246° C.

The base is liberated from an aqueous solution of the dihydrochloride by alkalizing with sodium hydroxide and extracting with chloroform. After drying the organic phase and evaporating, the crude base is obtained in a nearly quantitative yield and can be used as starting material in processes according to this Example.

EXAMPLE 28

8-(2,3-Dihydroxypropyl)-4-(4-ethoxycarbonyl-1-piperazinyl)-2-methyl-6,7-dihydro-8H-pyrimido[5,4-b][1,4]oxazin-7-one A suspension containing 0.96 g of 4-(4-ethoxycarbonyl-1-piperazinyl)-2-methyl-6,7-dihydro-8H-pyrimido[5,4-b][1,4]oxazin-7-one (Example 1), 0.44 g of 2,3-epoxy-1-propanol, 0.0966 g of tetra(n-butyl)-ammonium bromide and 20 ml of abs. benzene is boiled under stirring for 5 hours and left to stand at room temperature overnight. The crystals are filtered, washed with diisopropyl ethyl and dried to give 0.98 g (83%) of the product, m.p.: 146°–148° C.

EXAMPLE 29

4-(2-Hydroxyethyl)-amino-2-methyl-8-(2-oxopropyl)-6,7-dihydro-8H-pyrimido[5,4-b][1,4]oxazine-7-one 0.31 g of chloroacetone dissolved in 5 ml of methyl ethyl ketone is dropped to a suspension containing 0.68 g of 4-(2-hydroxyethyl)-amino-2-methyl-6,7-dihydro-8H-pyrimido[5,4-b][1,4]oxazin-7-one (Example 19), 0.5 g of anhydrous potassium carbonate and 15 ml of methyl ethyl ketone, then the mixture is boiled while stirring for 8 hours and filtered as hot. The filtrate is evaporated to 10 ml and left to stand at 0° to 4° C. overnight. The crystals are filtered, washed with ether and dried to give 0.70 g (83%) of the product, m.p.: 150°–152° C. The hydrochloride melts at 185°–187° C.

EXAMPLE 30

8-Cyanomethyl-2-methyl-4-[2-(4-morpholinyl)-ethyl]-amino-6,7-dihydro-8H-pyrimido[5,4-b][1,4]oxazin-7-one 0.25 g of chloroacetonitrile dissolved in 50 ml of methyl ethyl ketone is dropped within 15 minutes to a suspension containing 0.88 g of 2-methyl-4-[2-(4-morpholinyl)-ethyl]-amino-6,7-dihydro-8H-pyrimido[5,4-b][1,4]oxazin-7-one base (e.g. prepared as described in Example 23) and 0.5 g of anhydrous potassium carbonate in 15 ml of methyl ethyl ketone under boiling and stirring. The mixture is further boiled under stirring for 8 hours, the precipitate is filtered as hot and washed with methyl ethyl ketone. The filtrate is evaporated and the residue is triturated with diisopropyl ether. After filtering, the solid is washed with diisopropyl ether and dried to give 0.91 g (91%) of the product, m.p.: 126°–128° C.

EXAMPLE 31

8-aminocarbonylmethyl-4-(4-ethoxycarbonyl-1-piperazinyl)-2-methyl-6,7-dihydro-8H-pyrimido[5,4-b][1,4]oxazin-7-one A suspension containing 0.96 g of 4-(4-ethoxycarbonyl-1-piperazinyl)-2-methyl-6,7-dihydro-8H-pyrimido[5,4-b][1,4]oxazin-7-one (Example 1), 25 ml of methyl ethyl ketone, 0.5 g of anhydrous potassium carbonate and 0.31 g of chloroacetamide is boiled under stirring for 8 hours, filtered as hot, washed with methyl ethyl ketone and this filtrate is set aside. The precipitate is washed with water, then with ether and dried to give 0.65 g of the product, m.p.: 225°–227° C.

The above filtrate is evaporated to 10 ml and kept at 0° to 4° C. overnight. The crystals are filtered, washed and dried to give additional 0.20 g of the product, m.p.: 225°–227° C. (the total yield is 75%).

EXAMPLE 32

4-Chloro-8-ethoxycarbonylmethyl-2-methyl-6,7-dihydro-8H-pyrimido[5,4-b][1,4]oxazin-7-one A solution of 0.41 g of ethyl chloroacetate in 5 ml of methyl ethyl ketone is dropped to a mixture containing 0.6 g of 4-chloro-2-methyl-6,7-dihydro-8H-pyrimido[5,4-b][1,4]oxazin-7-one, 0.5 g of anhydrous potassium carbonate and 15 ml of methyl ethyl ketone within 15 minutes under refluxing and stirring. Then the mixture is refluxed under stirring for 8 hours, filtered as hot and washed with methyl ethyl ketone. The filtrate is evaporated to 10 ml, cooled and the unchanged starting material is filtered out. The mother liquor is evaporated, the residue is triturated with n-hexane, the solid precipitate is filtered, washed with n-hexane and dried to give 0.59 g (68%) of product, m.p.: 69°–70° C.

The compounds of Table 5 were essentially prepared by the methods described in Examples 28 to 32.

TABLE 5

Compounds of the formula (I), wherein $R^1$ means methyl group

| Example No. | $R^2$ | $R^3$ | $R^4$ | $R^9$ | Method type ex. No. | Yield % | M.p. °C. |
|---|---|---|---|---|---|---|---|
| 33 | Cl | H | H | CH$_2$CN | 30 | 79 | 147–149 |
| 34 | Cl | H | H | CH$_2$COCH$_3$ | 29 | 76 | 105–107 |
| 35 | Cl | CH$_3$ | CH$_3$ | CH$_2$CN | 32 | 80 | 110–111 |
| 36 | 2-Hydroxyethylamino | H | H | CH$_2$CN | 30 | 99 | 138–140 |
| 37 | 2-Hydroxyethylamino | H | H | CH$_2$CO$_2$C$_2$H$_5$ | 32 | 73 | 185–187* |
| 38 | 2-Hydroxyethylamino | H | H | CH$_2$CH(OH)CH$_2$OH | 28 | 99 | 128–131 |
| 39 | 2-Hydroxyethylamino | H | H | CH$_2$CONH$_2$ | 31 | 48 | 222–224 |
| 40 | N—Methyl-N—(2-hydroxyethyl)-amino | H | H | CH$_2$CN | 30 | 96 | 90–92 |
| 41 | N—Methyl-N—(2-hydroxyethyl)-amino | H | H | CH$_2$CO$_2$C$_2$H$_5$ | 32 | 63 | 134–137* |
| 42 | N—Methyl-N—(2-hydroxyethyl)-amino | H | H | CH$_2$COCH$_3$ | 29 | 39 | 190–192 |
| 43 | N—Methyl-N—(aminocarbonylmethyl)-amino | H | H | CH$_2$CO$_2$C$_2$H$_5$ | 32 | 25 | 142–145 |
| 44 | Cl | H | H | CH$_2$CONH$_2$ | 31 | 66 | 253–255 |
| 45 | 4-Morpholinyl | H | H | CH$_2$CH | 30 | 69 | 158–161 |
| 46 | 4-Morpholinyl | H | H | CH$_2$CO$_2$C$_2$H$_5$ | 32 | 75 | 117–119 |
| 47 | 2-(4-Morpholinyl)-ethylamino | H | H | CH$_2$COCH$_3$ | 29 | 85 | 148–150 |
| 48 | 2-(4-Morpholinyl)-ethylamino | H | H | CH$_2$CO$_2$C$_2$H$_5$ | 32 | 77 | 176–180* |
| 49 | 4-(2-Hydroxyethyl)-1-piperazinyl | H | H | CH$_2$COC$_2$H$_5$ | 32 | 69 | 125–128 |
| 50 | 4-Ethoxycarbonyl-1-piperazinyl | H | H | CH$_2$CN | 30 | 80 | 194–196 |
| 51 | 4-Ethoxycarbonyl-1-piperazinyl | H | H | CH$_2$COCH$_3$ | 29 | 76 | 143–145 |
| 52 | 4-Ethoxycarbonyl-1-piperazinyl | H | H | CH$_2$CO$_2$C$_2$H$_5$ | 32 | 79 | 105–106 |
| 53 | (2-Benzo[1,4]dioxanyl)-methylamino | H | H | CH$_2$CH(OH)CH$_2$OH | 28 | 28 | 200–201 |
| 54 | N—Benzyl-N—(2-hydroxyethyl)-amino | H | H | —CH$_2$CN | 30 | 40 | 100–103 |

TABLE 5-continued

Compounds of the formula (I), wherein $R^1$ means methyl group

| Example No. | $R^2$ | $R^3$ | $R^4$ | $R^9$ | Method type ex. No. | Yield % | M.p. °C |
|---|---|---|---|---|---|---|---|
| 55 | N—Benzyl-N—(2-hydroxyethyl)-amino | H | H | CH$_2$CH(OH)CH$_2$OH | 28 | 57 | 99–103* |

Note:
*Hydrochlodride

EXAMPLE 56

4-Chloro-8-(2,3-dihydroxypropyl)-2-methyl-6,7-dihydro-8H-pyrimido[5,4-b][1,4oxazin-7-one A mixture containing 10 g of 4-chloro-2-methyl-6,7-dihydro-8H-pyrimido[5,4-b][1,4]oxazin-7-one, 0.7 g of triethylamine hydrochloride, 7.4 of 2,3-epoxypropanol and 300 ml of abs. benzene is refluxed for 4 hours under stirring. Then the solution is washed with water and the organic phase is extracted with chloroform. After drying the chloroformic phase, the solvent is evaporated, the oily residue is taken up in chloroform and mixed with a 1:1 mixture of ether and petroleum ether. The precipitated oil soon crystallizes. After filtering, it is washed with petroleum ether and dried to give 5.21 g (38%) of the product, m.p.: 117°–118° C.

EXAMPLE 57

8-(2,3-Dihydroxypropyl)-2-methyl-4-(4-morpholinyl)-6,7-dihydro-8H-pyrimido[5,4-b][1,4]oxazin-7-one A mixture containing 1 g of 2-methyl-4-(4-morpholinyl)-6,7-dihydro-8H-pyrimido[5,4-b][1,4]oxazin-7-one, 0.59 g of 2,3-epoxypropanol, 0.128 g of tetra(n-butyl)ammonium bromide and 60 ml of abs. benzene is refluxed under stirring for 7 hours. After filtering, the precipitate is washed with benzene and ether and dried to give 1.04 g (77%) of the product, m.p.: 153°–155° C.

EXAMPLE 58

8-(2,3-Dihydroxypropyl)-2-methyl-4-[2-(4-morpholinyl)-ethyl]-amino-6,7-dihydro-8H-pyrimido[5,4-b][1,4]oxazin-7-one dihydrochloride A mixture containing 1 g of 2-methyl-4-[2-(4-morpholinyl)-ethyl]-amino-6,7-dihydro-8H-pyrimido[5,4-b][1,4]oxazin-7-one base (e.g. of Example 23), 0.57 of 2,3-epoxypropanol, 0.11 g of tetra(n-butyl)ammonium bromide and 40 ml of abs. benzene is refluxed under stirring for 8 hours. Then the benzene solution is washed with water, the aqueous phase is extracted with chloroform or with ethyl acetate, and the combined organic phase is dried and evaporated. The residue is dissolved in abs. ethanol and a calculated amount of ethanolic hydrogen chloride solution is added. After cooling, the precipitate is filtered, washed and dried to give 0.45 g (30%) of the product, m.p.: 158°–160° C.

EXAMPLE 59

8-(2,3-Dihydroxypropyl)-2-methyl-6,7-dihydro-8H-pyrimido[5,4-b][1,4]oxazin-7-one The solution of 2 g of γchloro-8-(2,3-dihydroxypropyl)-2-methyl-6,7-dihydro-8H-pyrimido[5,4-b][1,4]oxazin-7-one and 0.739 g of triethylamine in 50 ml of abs. ethanol is hydrogenated in the presence of 0.20 g of 5% palladium-on-charcoal catalyst at room temperature and atmospheric pressure. Then the catalyst is filtered out, the filtrate is evaporated, the residue is taken up in water and extracted with chloroform. The organic phase is dried and evaporated. The residue is triturated with petroleum ether and dried to give 0.33 g (19%) of the product, m.p.: 70°–72° C.

EXAMPLE 60

2-Methyl-4-[3-(4-morpholinyl)-1-propyl]-amino-6,7-dihydro-8H-pyrimido[5,4-b][1,4]oxazin-7-one A mixture of 0.7 ml of triethylamine and 1.44 g of 3-(4-morpholinyl)-1-propylamine is added in the course of 8 hours to a mixture containing 2 g of 4-chloro-2-methyl-6,7-dihydro-8H-pyrimido[5,4-b][1,4]oxazin-7-one and 1.4 ml of triethylamine in 5 ml of abs. benzene while stirring and refluxing. Then the mixture is refluxed under stirring for 8 hours, evaporated, the residue is taken up with 16 ml of water, triturated, filtered and washed with water and ether to give 1.1 g (36%) of the aimed product, m.p.: 165°–168° C.

The hydrochloride, m.p.: 250°–251° C., is obtained by adding ethanolic hydrogen chloride solution to the base dissolved in ethyl acetate.

EXAMPLE 61

4-Chloro-2-methyl-8-(3-pyridylmethyl)-6,7-dihydro-8H-pyrimido[5,4-b][1,4]oxazin-7-one The base liberated from 1 g of 3-chloromethylpyridine hydrochloride and dissolved in 5 ml of methyl ethyl ketone is dropped to the mixture containing 4-chloro-2-methyl-6,7-dihydro-8H-pyrimido[5,4-b][1,4]oxazin-7-one, 15 ml of methyl ethyl ketone and 0.83 g of anhydrous potassium carbonate while stirring.

The suspension is refluxed while stirring for 8 hours, filtered as hot and evaporated. The residue is triturated with diisopropyl ether and filtered to give 0.97 g (66%) of the product, m.p.: 116°–118° C. The hydrochloride melts at 220°–224° C.

EXAMPLE 62

4-(2-Hydroxyethyl)-amino-2,6,6-trimethyl-6,7-dihydro-8H-pyrimido[5,4-b][1,4]oxazin-7-one This compound is prepared similarly to Example 2 in a yield of 83%, m.p.: 168°–170° C. The hydrochloride melts at 190°–191° C.

EXAMPLE 63

8-Ethoxycarbonylmethyl-4-(2-hydroxyethyl)amino-2,6-dimethyl-6,7-dihydro-8H-pyrmido[5,4-b][1,4]oxazin-7-one hydrochloride This compound is prepared similarly to Example 32 in a yield of 41%, m.p.: 105°–108° C.

EXAMPLE 64

2,6-Dimethyl-4-(1-methyl-2-phenylethyl)-amino-6,7-dihydro-8H-pyrimido[5,4-b][1,4]oxazin-7-one This compound is prepared similarly to Example 2 in a yield of 31%, m.p.: 126°–130° C. The hydrochloride melts at 181°–184° C.

EXAMPLE 65

2,6-Dimethyl-8-(1-ethoxycarbonyl-1-ethyl)-4-(4-morpholinyl)-6,7-dihydro-8H-pyrimido[5,4-b][1,4]oxazin-7-one Starting from 4-chloro-2,6-dimethyl-6,7-dihydro-8H-pyrimido[5,4-b][1,4]oxazin-7-one (Khim. Geterotsikl. Soed. 1972, 1285) and ethyl 2-bromopropionate, Example 32 is followed. After refluxing for 12 hours and evaporating, the residue [the most part of which is 4-chloro-2,6-dimethyl-(1-ethoxycarbonyl-1-ethyl)-6,7-dihydro-8H-pyrimido[5,4-b][1,4]oxazin-7-one] is reacted with morpholine and worked up as described in Example 1, except that the evaporation residue is triturated with ether, filtered, the filtrate is evaporated and the residue is recrystallized from n-hexane to give the product in a yield of 42%, m.p.: 80°–82° C.

EXAMPLE 66

4-(2-Hydroxyethyl)-amino-2-methyl-8-(4-morpholinylcarbonyl)-methyl-6,7-dihydro-8H-pyrimido[5,4-b][1,4]oxazin-7-one This compound is prepared similarly to Example 32 in a yield of 89%, m.p.: 162°–165° C.

EXAMPLE 67

8-(n-Butoxycarbonyl)methyl-4-(2-hydrocyethyl)amino-2-methyl-6,7-dihydro-8H-pyrimido[5,4-b][1,4]oxazin-7-one hydrochloride This compound is prepared similarly to Example 32 in a yield of 62%, m.p.: 142°–145° C.

EXAMPLE 68

4-(4-Chlorobenzyl)-amino-2,6-dimethyl-8-ethoxycarbonylmethyl-6,7-dihydro-8H-pyrimido[5,4-b][1,4]oxazin-7-one This compound is prepared similarly to Example 32 in a yield of 62%, m.p.: 101°–104° C.

EXAMPLE 69

8-Benzyl-2-methyl-4-(2-hydroxyethyl)-amino-2-methyl-6,7-dihydro-8H-pyrimidino[5,4-b][1,4]oxazin-7-one This compound is prepared similarly to Example 1 in a yield of 84%, m.p.: 124°–126° C. The hydrochloride melts at 153°–157° C.

EXAMPLE 70

4-Hydrazino-2-methyl-6,7-dihydro-8H-pyrimido[5,4-b][1,4]oxazin-7-one 12.8 ml of 98% hydrazine hydrate dissolved in 40 ml of n-butanol are dropped to a solution of 20 g of 4-chloro-2-methyl-6,7-dihydro-8H-pyrimido[5,4-b][1,4]oxazin-7-one in 320 ml of n-butanol at 117° C. within 30 minutes while stirring. The mixture is stirred for an additional 45 minutes at 117° C., then cooled to room temperature. The precipitate is filtered and washed with water to give 11.66 g (56.3%) of the product, m.p.: 262°–264° C.

EXAMPLE 71

4-Azido-2-methyl-6,7-dihydro-8H-pyrimido[5,4-b][1,4]oxzazin-7-one 4.90 g of the product of Example 70 is suspended in 55 ml of water and 90 ml of glacial acetic acid and 1.75 g of sodium nitrite dissolved in 14 ml of water is dropwise added at 0° to 5° C. while stirring. The mixture is stirred at 5° C. for 20 minutes and at room temperature for 30 minutes. The precipitate is filtered, successively washed with water, ethanol and ether and dried to give 4.80 g (93.2%) of the product, m.p.: 214°–217° C.

EXAMPLE 72

4-Amino-2-methyl-6,7-dihydro-8H-pyrimido[5,4-b][1,4]oxazin-7-one hydrochloride 25 ml of 20% hydrochloric acid kept at 10° C. are dropped to a suspension of 4.0 g of 2-methyl-4-(triphenylphosphoranylidene)-imino-6,7-dihydro-8H-pyrimido[5,4-b][1,4]oxazin-7-one in 25 ml of ethanol within 15 minutes under stirring. The mixture is stirred at room temperature for 5 hours, the precipitate is filtered, washed with ethanol and dried to give 1.80 g (91%) of the hydrochloride melting above 260° C.

The base can be liberated from the hydrochloride by adding aqueous sodium hydrogen carbonate solution.

2-Methyl-4-(triphenylphosphoranylidene)-imino-6,7-dihydro-8H-pyrimido[5,4-b][1,4]oxazin-7-one, used as starting material, can be prepared as follows.

3.50 g of 4-azido-2-methyl-6,7-dihydro-8H-pyrimido[5,4-b][1,4]oxazin-7-one (Example 71) are portioned within 20 minutes to a solution of 4.48 g of triphenylphosphine in 140 ml of dry dichloromethane at room temperature under stirring. The mixture is stirred overnight, filtered and the solution is evaporated. The residue is suspended in 70 ml of ether, the precipitate is filtered and dried to give 6.75 g (95%) of product, m.p.: 245° C.

EXAMPLE 73

4-Amino-8-ethoxycarbonylmethyl-2-methyl-6,7-dihydro-8H-pyrimido[5,4-b][1,4oxazin-7-one A suspension containing 0.90 g of 4-amino-2-methyl-6,7-dihydro-8H-pyrimido[5,4-b][1,4-oxazin-7-one, 0.69 g of anhydrous potassium carbonate and 0.65 ml of ethyl chloroacetate in 20 ml of methyl ethyl ketone is refluxed for 20 hours. The inorganic salts are filtered out, the filtrate is evaporated and the residue is recrystallized from isopropanol to give 0.43 g 32.3% of the product, m.p.: 149°–150° C. From the mother liquor, additional 0.22 g (16.2%) of the product can be isolated.

EXAMPLE 74

Preparation of tablets

| Composition (for 1000 tablets) | g |
|---|---|
| Fumarate of the base described in Example 22 | 10 |
| Lactose | 185 |
| Microcrystalline cellulose | 25 |
| Talc | 5 |
| Corn starch | 73 |
| Magnesium stearate | 2 |
| Total: | 300 |

The above ingredients are mixed, homogenized and compressed to tablets containing 10 mg of the active ingredient each.

EXAMPLE 75

Preparation of an injectable solution

| Composition (for 2 liters of solution) | |
|---|---|
| Fumarate of the base described in Example 22 | 2 g |
| Sodium chloride | 20 g |
| water for injection purposes q.s. ad | 2000 ml |

The mixture is filled as divided into ampoules containing 2 ml of the solution each.

We claim:

1. A compound of the Formula (I),

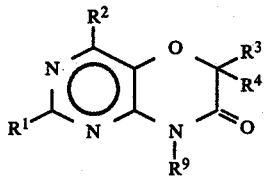

wherein $R^1$ stands for a $C_{1-4}$ alkyl group;

$R^2$ stands for halogen or an $-NR^5R^6$ group, wherein $R^5$ represents hydrogen or a benzyl group $R^6$ stands for hydrogen, a straight or branched-chain $C_{1-4}$ alkyl group optionally substituted by a hydroxyl, di($C_{1-4}$ alkyl)amino group or by a 6-membered, saturated nitrogen-containing heterocycle optionally containing an additional nitrogen or oxygen atom and optionally substituted by a methyl or benzyl group; further $NR^5R^6$ may also represent a 6-membered, saturated nitrogen-containing heterocycle optionally containing an additional nitrogen or oxygen atom and optionally substituted by a $C_{2-4}$ alkoxycarbonyl or $C_{1-4}$ hydroxyalkyl group;

$R^3$ and $R^4$ are the same or different and stand for hydrogen or a methyl group;

$R^9$ stands for hydrogen or a $C_{1-3}$ alkyl group unsubstituted or monosubstituted by an oxo, cyano, $C_{2-5}$ alkoxycarbonyl, morpholinocarbonyl, or phenyl group or mono- or polysubstituted by a OH group, with the proviso that $R^2$ is different from a chlorine, 4-morpholinyl or piperidyl group when $R^9$ stands for hydrogen; or $R^2$ is different from a chlorine or 4-morpholinyl group when $R^9$ stands for a methyl or benzyl group, or a tautomer, tautomeric mixture or pharmaceutically acceptable acid addition salt thereof.

2. The compound of the Formula (I) defined in claim 1 wherein $R^1$ is methyl, or a tautomer, tautomeric mixture, or pharmaceutically acceptable acid addition salt thereof.

3. The compound of the Formula (I) defined in claim 1 wherein $R^2$ is $-NR^5R^6$ and $-NR^5R^6$ is 4-morpholinyl, or a tautomeric, tautomeric mixture or pharmaceutically acceptable acid addition salt thereof.

4. The compound of the Formula (I) defined in claim 1 wherein $R^2$ is $-NR^5R^6$, $R^5$ is hydrogen and $R^6$ is selected from the group consisting of 2-(4-morpholinyl)-ethyl, (4-benzyl-2-morpholinyl)-methyl and 3-(4-morpholinyl)-propyl, or a tautomer, tautomeric mixture, or pharmaceutically acceptable acid addition salt thereof.

5. A compound selected from the group consisting of
2-methyl-4-[2-(4-morpholinyl)-ethyl]-6,7-dihydro-8H-pyrimido[5,4-b][1,4]oxazin-7-one,
4-[N-benzyl-N-(2-hydroxyethyl)]-amino-2-methyl-6-7-dihydro-8H-pyrimido[5,4-b][1,4]oxazin-7-one,
2-methyl-4-[3-(4-morpholinyl)-propyl]-amino-6,7-dihydro-8H-pyrimido[5,4-b][1,4]oxazin-7-one,
4-chloro-8-(2,3-dihydroxypropyl)-2-methyl-6,7-dihydro-8H-pyrimido[5,4-b][1,4]oxazin-7-one,
8-(2,3-dihydroxypropyl)-2-methyl-4-(4-morpholinyl)-6,7-dihydro-8H-pyrimido[5,4-b][1,4]-oxazin-7-one,
4-[(4-benzyl-2-morpholinyl)-methyl]-amino-2-methyl-6,7-dihydro-8H-pyrimido[5,4-b][1,4]oxazin-7-one,
8-ethoxycarbonylmethyl-4-(2-hydroxyethyl)-amino-2-methyl-6,7-dihydro-8H-pyrimido[5,4-b][1,4]oxazin-7-one,
4-(2-hydroxyethyl)-amino-2-methyl-8-(2-oxopropyl)-6,7-dihydro-8H-pyrimido[5,4-b][1,4]oxazin-7-one,
4-(2-hydroxyethyl)-amino-2-methyl-8-(4-morpholinylcarbonyl)-methyl-6,7-dihydro-8H-pyrimido[5,4-b][1,4]-oxazin-7-one,
8-(n-butoxycarbonyl)-methyl-4-(2-hydroxyethyl)-amino-2-methyl-6,7-dihydro-8H-pyrimido[5,4-b][1,4]-oxazin-7-one,
8-benzyl-4-(2-hydroxyethyl)-amino-2-methyl-6,7-dihydro-8H-pyrimido[5,4-b][1,4]oxazin-7-one, and
4-amino-8-ethoxycarbonylmethyl-2-methyl-6,7-dihydro-8H-pyrimido[5,4-b][1,4]oxazin-7-one or a tautomer, tautomeric mixture or a pharmaceutically acceptable acid addition salt thereof.

6. 2-methyl-4-[2-(4-morpholinyl)-ethyl]-amino-6,7-dihydro-8H-pyrimido[5,4-b][1,4]oxazin-7-one or the dihydrochloride or fumarate thereof as defined in claim 5.

7. A pharmaceutical composition which comprises as active ingredient a compound of the formula (I), as defined in claim 1, or a pharmaceutically acceptable acid addition salt thereof in admixture with carriers and/or additives commonly used in the pharmaceutical industry.

8. A method of treating chronic heart failure or coronary disturbances in a mammalian subject which comprises the step of administering to said mammalian subject a therapeutically effective amount of a compound of the Formula (I)

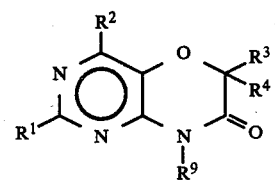

wherein $R^1$ stands for a $C_{1-4}$ alkyl group;

$R^2$ stands for hydrogen or halogen or an azido group or an $-NR^5R^6$ group, wherein $R^5$ represents hydrogen or a benzyl group or a $C_{1-4}$ alkyl group unsubstituted or substituted by a hydroxyl group, $R^6$ stands for hydrogen, an amino group, a $C_{3-6}$ cycloalkyl group, a straight or branched-chain $C_{1-4}$ alkyl group optionally substituted by a hydroxyl, mercapto, aminocarbonyl, furyl, 2-benzo[1,4]-dioxanyl, di($C_{1-4}$ alkyl)amino group or by a phenyl or phenoxy group optionally mono- or polysubstituted by halogen or $C_{1-4}$ alkoxy group(s) or by a 6-membered, saturated nitrogen-containing heterocycle optionally containing an additional nitrogen or oxygen atom and optionally substituted by a $C_{1-4}$ alkyl or benzyl group; further $NR^5R^6$ may also represent a 6-membered, saturated nitrogen-containing heterocycle optionally containing an additional nitrogen or oxygen atom and optionally substituted by a $C_{2-4}$ alkoxycarbonyl or $C_{1-4}$ hydroxyalkyl group;

$R^3$ and $R^4$ are the same or different and stand for hydrogen or a $C_{1-4}$ alkyl group;

$R^9$ stands for hydrogen or a $C_{1-4}$ alkyl group unsubstituted or monosubstituted by an oxo, cyano, aminocarbonyl, $C_{2-5}$ alkoxycarbonyl, pyridyl, morpholinocarbonyl, or phenyl group or mono- or polysubstituted by OH group(s), with the proviso that $R^2$ is different from chlorine, 4-morpholinyl and piperidyl group when $R^9$ stands for hydrogen; or $R^2$ is different from chlorine and 4-morpholinyl group when $R^9$ stands for a methyl or benzyl group, or a tautomer, tautomeric mixture, or pharmaceutically acceptable acid addition salt thereof.

9. The method of treatment defined in claim 8 wherein the compound of the Formula (I) or a tautomer, tautomeric mixture or pharmaceutically acceptable acid addition salt thereof is enterally administered.

10. The method of treatment defined in claim 8 wherein the compound of the Formula (I) or a tautomer, tautomeric mixture or pharmaceutically acceptable acid addition salt thereof is parenterally administered.

* * * * *